United States Patent [19]

Mandle et al.

[11] 4,372,745

[45] Feb. 8, 1983

[54] CHEMICAL LUMINESCENCE AMPLIFICATION SUBSTRATE SYSTEM FOR IMMUNOCHEMISTRY INVOLVING MICROENCAPSULATED FLUORESCER

[75] Inventors: Richard M. Mandle, Pompton Lakes; Yuan N. Wong, Boonton, both of N.J.

[73] Assignee: Electro-Nucleonics, Inc., Fairfield, N.J.

[21] Appl. No.: 233,057

[22] Filed: Feb. 10, 1981

Related U.S. Application Data

[63] Continuation-in-part of Ser. No. 105,257, Dec. 19, 1979, abandoned.

[51] Int. Cl.$^3$ .................... G01N 33/54; G01N 33/58; G01N 33/52
[52] U.S. Cl. .................... 436/537; 252/316; 422/61; 436/800; 436/805; 436/808; 436/826
[58] Field of Search .................... 23/230 B; 424/8, 12; 422/61; 252/316

[56] References Cited

U.S. PATENT DOCUMENTS

| | | | |
|---|---|---|---|
| 3,401,123 | 9/1968 | Brynko | 252/316 |
| 3,597,362 | 8/1971 | Bollyky | |
| 3,700,738 | 10/1972 | Bysouth | |
| 3,704,231 | 11/1972 | Bollyky | |
| 3,817,837 | 6/1974 | Rubenstein | |
| 3,887,698 | 6/1975 | McConnel | 424/12 |
| 3,935,074 | 1/1976 | Rubenstein | 424/12 X |
| 4,011,219 | 3/1977 | Nishii | 544/237 |
| 4,018,884 | 4/1977 | Cleeland | 424/8 |
| 4,020,151 | 4/1977 | Bolz | 23/230 B X |
| 4,104,029 | 8/1978 | Maier | 23/230 B |
| 4,153,675 | 5/1979 | Kleinerman | 424/8 |
| 4,160,818 | 7/1979 | Smith | 424/8 |
| 4,169,137 | 9/1979 | Hirshfeld | 424/8 |
| 4,193,983 | 3/1980 | Ullman | 435/7 X |
| 4,199,559 | 4/1980 | Ullman | 424/8 |
| 4,201,763 | 5/1980 | Monthony | 424/8 |
| 4,235,792 | 11/1980 | Hsid | 424/12 X |
| 4,235,871 | 11/1980 | Papahadjopoulos | 424/19 |
| 4,241,046 | 12/1980 | Papahadjopoulos | 424/19 |
| 4,255,411 | 3/1981 | Lim | 23/230 B X |
| 4,280,816 | 7/1981 | Elahi | 23/230 B |
| 4,326,008 | 4/1982 | Rembaum | 424/12 X |
| 4,342,739 | 8/1982 | Kakimi | 424/12 X |
| 4,342,826 | 8/1982 | Cole | 424/12 X |

FOREIGN PATENT DOCUMENTS

1461877 1/1977 United Kingdom .

OTHER PUBLICATIONS

Chemical Abstracts, 93:236756x (1980).
*Chem. Abstracts,* vol. 88, 1978, pp. 277, 16637 0n—Detection and Analysis of Small Amounts of Organic Materials in Body Fluids.
*Analytical Chemistry,* vol. 50, No. 8, Jul., 1978, pp. 1026-1031, W. J. Blaedel et al. Chemical Amplification in Analysis: A Review.
*Analytical Chemistry,* vol. 50, No. 8, Jul. 1978, pp. 1032-1040, J. A. Campbell et al. Separation and Chemical Characterization of Finely-Size Fly-Ash Particles.
*Clin. Chem.* 25/4, 512-519 (1979), Frans Gorus et al. Applications of Bio- and Chemiluminescence in the Clinical Laboratory.
*Journal of Chromotography,* 134(1977) 343-350, Tommie G. Curtis et al. Chemiluminescence: A New Method for Detecting Fluorescent Compounds Separated by Thin-Layer Chromatography.
*Anal. Chim. Acta,* 97 (1978) 21, Rasherman et al, Chemical Applications of Peroxyoxalate Chemiluminescence.
*Nature,* vol. 279, Jun. 14, 1979, pp. 646-647, A Stable Chemiluminescent-Labelled Antibody for Immunological Assays.
*Analytical Biochemistry,* 93, 267-271 (1979), Leroy S. Hersh et al., A Luminol-Assisted, Competitive-Binding Immunoassay of Human Immunoglobulin G.
M. M. Rauhut, vol. 2, Mar. 1969, pp. 80-87, Chemiluminescence from Concerted Peroxide Decomposition Reactions.
*Journal of the American Chemical Society,* 89:25, Dec. 6, 1967, pp. 6523-6526, L. J. Bollyke et al. Chemiluminescence from Reactions of Oxalic Anhydrides with Hydrogne Peroxide in the Presence of Fluorescent Compounds.
*Analytical Chemistry,* vol. 48, No. 11, Sep. 1976, pp. 1478-1481, David C. William III et al. Automated Chemiluminescence Method for Determining the Reduced Form of Nicotinamide Adenine Dinucleotide Coupled to the Measurement of Lactate Dehydrogenase Activity.
*Tab. 1 Reaktionprodukte des Anthrachinon vom Typ,* Jahrg. 94, 1961, pp. 1051-1058, Walter Ried et al. Mono- and Dianlagerungen von Monosubstituierten Acetylendervaten an usubstituiertes und substituierties Anthrachinon.
*A Synthesis of Rubrene,* by C. F. H. Allen et al., Jun. 1936, pp. 37-940, vol. 58.
*Analytical Chemistry,* vol. 48, No. 7, Jun. 1976, pp. 1003-1006, David C. Williams III et al. Evaluation of Peroxyoxalate Chemiluminescence for Determination of Enzyme Generated Peroxide.
*Journal of the American Chemical Society,* 89:25, Dec. 6, 1967, M. M. Rauhut et al., Chemiluminescence from Reactions of Electronegatively Substituted Aryl Oxalates with Hydrogen.
*Journal of Chemical Education,* vol. 51, No. 8, Aug. 1974, pp. 528-529, Arthur G. Mohan et al. A Facile and Effective Chemiluminescence Demonstration Experiment.
*Clinical Chemistry,* vol. 231, No. 9, 1975, pp. 1225-1233, C. A. Burtiss et al. Development of a Multipurpose Optical System for Use with a Centrifugal Fast Analyzer.
*Photochemistry and Photobiology,* 1968, vol. 8, pp. 383-392, Pergamon Press, Printed in Great Britain, J. S. Bellin Photophysical and Phototchemical Effects of Dye Binding.
*Contribution from the Chemical Laboratory of the Ohio State University,* pp. 618-622, Melvin S. Newman et al. The Orientation of Chrysene.
*Notes,* pp. 2909-2910, vol. 609, Nov., 1947, M. Kasha et al. On the Correlation of the Spectroscopic and Thermal Energy Differences Between the Fluorescence and Phosphorescence Levels of Dye Molecules.
*Journal of Chromatography,* 81 (1973) 353, 356, Elsevier Scientific Publishing Company, Amsterdam, Printed in The Netherlands, Marc Roth et al. Column Chromatography of Amino Acids with Fluorescence Detection.
*Photochemistry and Photobiology,* 1965, vol. 4, pp. 1097, 1110, Pergamon Press Ltd., Printed in Great Britain, M. M. Rauhut et al. Structural Criteria for Chemiluminescence in Acyl Peroxide Decomposition Reactions.
*Photochemistry and Photobiology,* 1965, vol. 4, pp. 111, 1121, Pergamon Press Ltd., Printed in Great Britain, Frank McCapra et al. Chemiluminescence Involving Peroxide Decompositions.
*Proc. Nat. Acad. Sci.* US 72 (1975) pp. 619–622, Feb. 1975, James R. Benson et al. Phthalaaldehyde: Fluoregeneic Detection of Primary Amines in the Picomole Range, Comparison with Fluorescamine and Ninhydrin.
*Clin. Chemistry,* vol. 25, No. 7, 1970, p. 1350, Irwin Wieder, Correction to Fluorescence Immunoassay Review.
*Analytical Chemistry,* vol. 48, No. 7, Jun. 1976, pp. 545A–558A, Larry D. Bowers et al., Applications of Immobilized Enzymes.
*Chemtech.* Apr. 1976, pp. 219–220, A. Brownstein et al. Heart Cut.
*Analytical Chemistry,* vol. 48, No. 9, Aug. 1976, pp. 1403–1405, Richard Delumyea et al., Metal Catalysis of the Luminol Reaction in Chromatographic Solvent Systems.
*Analytical Chemistry,* vol. 48, No. 8, Jul. 1976, pp. 1188–1192, Paul R. Michael et al. Comparisons Between the Luminol Light Standards and a New Method for Absolute Calibrations of Light Detectors.
*Analytical Chemistry,* vol. 47, No. 2, Feb. 1975, John P. Auses et al. Chemiluminescent Enzyme Method for Glucose.
*Analytical Chemistry,* vol. 47, No. 2, Feb. 1975, pp. 249–255, Csaba P. Keszthelyi et al. Electrogenerated Chemiluminescence: Determination of the Absolute Luminescence Efficiency in Electrogenerated Chemiluminescence; 9,10-Diphenylanthracene-Thianthrene and Other Systems.
*Analytical Chemistry,* vol. 47, No. 2, Feb., 1975, R. Marshall Wilson et al., Computerized Kinetic Luminescence Spectrometry: Time-Resolved and Component-Resolved Phosphorenscence Spectrometry.
*Analytical Chimica Acta,* 68, (1974) 339–362, U. Isacsson et al. Chemiluminescence in Analytical Chemistry, Elsevier Publishing Co., Amsterdam, Printed in The Netherlands.
*Analytical Letters,* 7 (8 & 9), 583–590 (1974), Michael P. Neary et al. A Chemiluminescence Detector for Transition Metals Separated by Ion Exchange.
*Analytical Chemistry,* vol. 44, No. 13, Nov. 1974, pp. 2143–2149, W. Rudolf Seitz et al. Determination of Trace Amounts of Iron (II) Using Chemiluminescence Analysis.
*Analytical Chemistry,* vol. 44, No. 6, May 1972, pp. 957–963, W. Rudolph Seitz et al., Determination of Trace Amount of Chromium (III) Using Chemiluminescence Analysis.
*Analytical Chemistry,* vol. 46, No. 2, Feb., 1974, pp. 188A–202A, W. Rudolf Seitz et al., Chemiluminescence and Bioluminescence in Chemical Analysis.
*Analytical Chemistry,* vol. 43, No. 11, Sep. 1971, pp. 1438–1441, Michel Heurtebise et al., Application of an Iodide-Specific Resin to the Determination of Iodine in Biological Fluids by Activation Analysis.
*Analytical Chemistry,* vol. 40, No. 14, Dec. 1968, pp. 2194–2196, Joe A. Vison et al. Quantitative Determination of Organic Halides in Dimethyl Sulfoxide.
*Analytical Chemistry,* vol. 36, No. 6, May 1964, pp. 1138–1140, Ralph Grunewald et al. Large Volume Activation Analysis of Organically Bound Iodine Using Isotopic Neutron Sources.
*Analytical Chemistry,* vol. 47, No. 6, May 1975, pp. 915–916, Jack L. Lambert et al. Iodine and Iodine Determination in the Parts-per-Billion Range with Leuco Crystal Violet and N-Chlorosuccinimide Succinimide Reagents.
*Analytical Letters,* 7(1), 79–88 (1974), Arleigh Hartkopf et al., Use of the Luminol Reaction for Metal Ion Detection in Liquid Chromatography.
*Clinical Chemistry,* vol. 25, No. 9, 1979, pp. 1531–1546, Thomas P. Whitehead et al. Analytical Luminescence: Its Potential in the Clinical Laboratory.
*Journal of Immunological Methods,* 26 (1979), 229–244, James T. Sundeen et al. A Quantitative Assay for Low Levels of IgM by Solid-Phase Immunofluorescence.
*Journal of Immunological Methods,* 26 (1979), 307–313, pp. 307–313, R. D. Nargessi et al. Use of Antibodies Against the Label in Non-Separation Non-Isotopic Immunoassay: 'Indirect Quenching' Fluoroimmunoassay of Proteins.
*Journal of Immunological Methods,* 35 (1979), 127–135, pp. 127–135, Luminescence Immunoassay (LIA): A Solid-Phase Immunoassay Monitored by Chemiluminescence.
*Journal of Immunological Methods,* 25 (1979), 275–282, Hartmut R. Schroeder et al., Immunoassay for Serum Thyroxine Monitored by Chemiluminescence.
*Journal of Immunological Methods,* 21, (1978) 179 181, J. J. Pratt et al. Chemiluminescence-Linked Immunoassay.
*Applied and Environmental Microbiology,* Apr. 1978, pp. 813–816, vol. 35, No. 4, Carol A. Miller et al. Chemiluminescent Detection of Bacteria: Experimental and Theoretical Limits.
*Luminescence of Liquid and Solid and its Practical Applications,* by Peter Pringsheim and Marcel Vogel, Interscience Publishers, Inc. N.Y., 1946.
*Analytical Chemistry,* vol. 39, No. 11, Sep. 1967, pp. 1294–1297, Horacio A. Mottola et al. Use of Metal Ion Catalysis in Detection and Determination of Microamounts of Complexing Agents.

*Primary Examiner*—Sidney Marantz
*Attorney, Agent, or Firm*—Vincent J. Vasta, Jr.

[57] ABSTRACT

A system for the detection of a biological analyte of interest is disclosed which comprises a microencapsulated fluorescer material which has been conjugated to an immunological specie specific to the biological analyte of interest, a means of disrupting the capsule containing the fluorescer and an energy source other than electro-magnetic radiation which is capable of activating the fluorescer. A method for the qualitative and/or quantitative detection of a biological of interest is disclosed, which comprises:

(a) labeling an immunological specie specific to the analyte of interest with a microencapsulated fluorescer material which is biologically compatible with such specie;
(b) contacting the microencapsulated fluorescer labeled specie and the biological of interest to form a microencapsulated fluorescer labeled specie/biological complex;
(c) separating the microencapsulated fluorescer labeled specie/biological complex;
(d) distrupting the capsule containing the fluorescer label thus freeing it to solution;
(e) contacting the freed fluorescer with an energy source other than electro-magnetic radiation which is capable of activating the fluorescer label; and
(f) determining the presence of and/or measuring the quantity of chemiluminescent light emitted.

47 Claims, No Drawings

CHEMICAL LUMINESCENCE AMPLIFICATION SUBSTRATE SYSTEM FOR IMMUNOCHEMISTRY INVOLVING MICROENCAPSULATED FLUORESCER

CROSS REFERENCE TO RELATED APPLICATION

This application is a continuation-in-part of applicants copending application Ser. No. 105,257, abandoned, filed Dec. 19, 1979, the priority of which is hereby claimed.

This invention relates to a system for the detection of a biological analyte of interest which comprises a microencapculated fluorescer which has been conjugated to an immunological specie specific to the biological analyte of interest, a means for disrupting the microcapsule to free the fluorescer and an energy source other than electro-magnetic radiation which is capable of activating the fluorescer.

This invention also relates to a novel class of microencapsulated fluorescer materials which may be conjugated to an immunological specie specific to a biological analyte of interest to provide a means for the detection of such biological.

This invention also relates to novel microencapsulated fluorescer materials and conjugated microencapsulated fluorescer/immunological specie compositions useful in the detection of various biological analytes of interest.

This invention also relates to novel test kits for the detection of a biological analyte of interest employing the microencapsulated fluorescers described herein.

BACKGROUND OF THE INVENTION

The clinician is concerned with detecting the presence of, and quantitatively measuring, a variety of substances via the use of many different analytical techniques. The most commonly used techniques employ absorbtiometry, both at visible and ultraviolet wavelengths, however, emission, flame photometry and radioactivity are also commonly used. A novel technique, thus far relatively unexplored in chemistry, is that employing the phenomenon of luminescence.

Analyses based on the measurement of emitted light offer several distinct advantages over conventionally employed techniques, including high sensitivity, wide linear range, low cost per test, and relatively simple and inexpensive equipment.

It has been predicted that the phenomenon of luminescence, and more particularly chemiluminescence could have a major impact in two main areas of clinical analysis. First, it may have an important role as a replacement for conventional colorimetric or spectrophotometric indicator reactions in assays for substrates of oxidases and dehydrogenases. In this type of assay the sensitivity of the luminescence indicator reaction may be used to quantitate substrates not easily measured by conventional techniques (e.g., prostaglandins and vitamins).

The second major clinical application of luminescence must be in the utilization of luminescent molecules as replacements for radioactive or enzyme labels in immunoassay.

In each of these major clinical application areas, chemiluminescent reactions can provide a means to achieve a high level of analytical sensitivity.

Chemiluminescence may be simply defined as the chemical production of light. In the literature it is often confused with fluorescence. The difference between these two phenomena lies in the source of the energy which promotes molecules to an excited state. In chemiluminescence this source is the non-radiative energy yielded as the result of a chemical reaction. The subsequent decay of molecules from the excited state back to the ground state is accompanied by emission of light, which is called luminescence. In contrast, in fluorescence, incident radiation is the source of the energy which promotes molecules to an excited state.

From an analytical point of view, the types of luminescence that have engendered the most interest are chemiluminescence and bioluminescence. The latter being the name given to a special form of chemiluminescence found in biological systems, in which a catalytic protein increases the efficiency of the luminescent reaction. Bioluminescent reactions such as the enzymatic firefly process, have been very useful analytically and convert chemical energy to light with a quantum efficiency of 88%.

In contrast to bioluminescence with the longevity and efficiency of the firefly, the history of chemiluminescence (hereinafter referred to as CL), especially that occurring in the non-aqueous phase, is remarkably short. The important aqueous CL substances luminol and lucigenin were discovered in 1928 and 1935, respectively. A series of organic soluble CL materials were developed in the early 1960's based upon a study of the luminescent reactions of a number of oxalate compounds. A typical organic system useful for CL was disclosed by Bollyky et al., U.S. Pat. No. 3,597,362, and claimed to exhibit a quantum efficiency of about 23% compared with about 3% for the best known available aqueous systems.

Chemiluminescence has become increasingly attractive for its potential in the clinical laboratory, especially for use in the analysis of a number of biologically associated materials, and its known applications have been the subject of thorough reviews, see for example: Whitehead et al. (1979) Analytical Luminescence: Its potential In The Clinical Laboratory, *Clin. Chem.*, 25, 9 1531–1546; Gorus et al. (1979) Applications Of Bio- And Chemiluminescence In The Clinical Laboratory, *Clin. Chem.*, 25, 4 512–519; Isacsson et al. (1974) Chemiluminescence In Analytical Chemistry, *Analytical Chemica Acta,* 68, 339–362.

With few exceptions, most published CL clinical analytical applications have made use of the less efficient but well known diacylhydrazides, acridinium salts, pyrogallol, or lophine structures. It is important to appreciate that due to the nature of the chemical decomposition of the above chemiluminescent structures in the presence of hydrogen-peroxide, or generators of $H_2O_2$, as compared to that of the oxidation reaction of diaryloxalate structures, the latter has over 20 times the quantum yield of chemiluminescence, although its requirement for hydrogen peroxide is greater than the former.

Hydrogen peroxide, an essential component in many chemiluminescent reactions, has usually been the species selected for use in detecting the analyte of interest. For example, in the determination of glucose-Auses et al. (1975), Chemiluminescent Enzyme Method For Glucose. *Analytical Chemistry,* 47, No. 2, 244–248 employed the oxidation of glucose in the presence of glucose oxidase as the source of $H_2O_2$ which, in turn, was reacted with luminol to produce chemiluminescence in proportion to the initial glucose concentration. A limit of detection of $8 \times 10^{-9}$ M peroxide was obtained with this system. Williams et al. (1976), Evaluation Of Peroxyoxalate Chemiluminescence For Determination Of Enzyme Generated Peroxide. *Anal. Chem.*, 48, 7 1003–1006 in a similar reaction concluded the limit of sensitivity of the peroxyoxalate system is an order of magnitude poorer than that of the luminol system.

Therefore, until now the oxalic ester system (oxalate system) was generally thought to have little utility for analytical purposes due to its inefficient conversion of hydrogen peroxide.

In one embodiment the present invention overcomes the deficiency of $H_2O_2$ dependence by making use of the large chemiluminescent reservoir of energy in the oxalate system's chemistry. By using a suitable quantity of hydrogen peroxide and oxalate, a vast amount of energy may be generated in a form which is then released as chemiluminescence upon the introduction of a fluorescer.

Thus, the oxalate, acting in a fashion which can be visualized as analogous to a charged chemical battery, releases the stored energy to the fluorescer-conjugate in the same manner as an electrical switch in a circuit releases the energy of a battery to a lamp. This "switch" action causes chemiluminescence and, by incorporating the fluorescer to a detector of the analyte of interest, one can employ the reaction to trigger a detection system both qualitatively and quantitatively related to the analyte to be measured.

It is, therefore, an object of the present invention to provide for a system for the detection of a biological analyte of interest comprising an encapsulated fluorescer material which has been conjugated to an immunological specie specific to the biological analyte of interest, a means of disrupting the capsule containing the fluorescer and an energy source other than electro-magnetic radiation which is capable of activating the fluorescer.

A further object of the present invention is to provide for a qualitative method for the detection of a biological analyte of interest comprising:

(a) labeling an immunological specie specific to the analyte of interest with an encapsulated fluorescer material which is biologically compatible with such specie;

(b) contacting the encapsulated fluorescer labeled specie and the biological of interest to form an encapsulated fluorescer labeled specie/biological complex:

(c) separating the fluorescer labeled specie/biological complex;

(d) disrupting the capsule containing the fluorescer label thus freeing it to solution;

(e) contacting the freed fluorescer with an energy source other than electro-magnetic radiation which is capable of activating the fluorescer label; and (f) determining the presence or absence of chemiluminescent light emitted from the activated fluorescer.

A further object of the present invention is to provide for a quantitative method for measuring the amount of a biological analyte of interest comprising:

(a) labeling an immunological specie specific to the analyte of interest with an encapsulated fluorescer material which is biologically compatible with such specie;

(c) contacting the encapsulated fluorescer labeled specie and the biological of interest to form an encapsulated fluorescer labeled specie/biological complex;

(d) disrupting the capsule containing the fluorescer label thus freeing it to solution;

(e) contacting the freed fluorescer with an energy source other than electro-magnetic radiation which is capable of activating the fluorescer label; and (f) determining the presence or absence of chemiluminescent light emitted from the activated fluorescer.

A further object of the present invention is to provide for a novel class of micro encapsulated fluorescer materials which may be conjugated to an immunological specie specific to a biological analyte of interest to provide a means for the detection of such biological.

A further object of the present invention is to provide for a novel class of conjugated microencapsulated fluorescer/biological compositions useful in the detection of various biological analytes of interest.

A further object of the present invention is to provide for test kits for the detection of a biological analyte of interest employing the microencapsulated fluorescer materials described herein.

DESCRIPTION OF THE INVENTION

According to the present invention, there is provided a system for the detection of a biological analyte of interest comprising an encapsulated fluorescer material which has been conjugated to an immunological specie specific to the biological analyte of interest, a means for disrupting the capsule containing the fluorescer and an energy source other than electro-magnetic radiation which is capable of activating the fluorescer.

There is also provided a method for the qualitative and/or quantitative method for the detection of a biological of interest comprising:

(a) labeling an immunological specie specific to the analyte of interest with an encapsulated fluorescer material which is biologically compatible with such specie;

(b) contacting the encapsulated fluorescer labeled specie and the biological of interest to form an encapsulated fluorescer labeled specie/biological complex;

(c) separating the encapsulated fluorescer labeled specie/biological complex;

(d) disrupting the capsule containing the fluorescer label thus freeing it to solution;

(e) contacting the freed fluorescer with an energy source other than electro-magnetic radiation which is capable of activating the fluorescer label; and (f) detecting the presence of and/or measuring the quantum of chemiluminescent light emitted.

Additionally, there is provided novel microencapsulated fluorescer and conjugated microencapsulated fluorescer/immunological specie compositions useful in the detection of various biological analytes of interest.

Further there is provided novel test kits for the detection of a biological analyte of interest employing the microencapsulated fluorescer materials described.

With respect to Charts I, II, and III, Rauhut et al. (1969), Chemiluminescence From Concerted Peroxide Decomposition Reactions, *Accounts of Chemical Research*, Vol. 2, 80–87, it can be seen that one mole of $H_2O_2$ is necessary to convert one mole of luminol into one mole of the energized or excited molecule. This excited molecule then reverts to its ground state and emits light. Of interest is the fact that the CL compound, in Chart I, luminol or its derivatives, is also capable of converting the chemical energy of the system to light. Thus, the luminol acts as a source of CL energy and also as a fluorescer to absorb the energy and produce visible light. The luminol system is, therefore, not particularly useful in the context of the present invention since no differentiation between the light emitted upon fluorescer addition and that generated by the luminol itself can be made.

Charts II and III illustrate the fact that for the oxalate system, hydrogen peroxide does not always produce a species which gives rise to an excited state producing light. Some peroxide may be lost in side reactions which are "dark", thus, there is no predictable stoichiometric relationship between the $H_2O_2$ consumption and the quanta of emitted light.

CHART I

3-Aminophthalhydrazide Chemiluminescence in Reaction with Potassium Persulfate and Hydrogen Peroxide (Luminol)

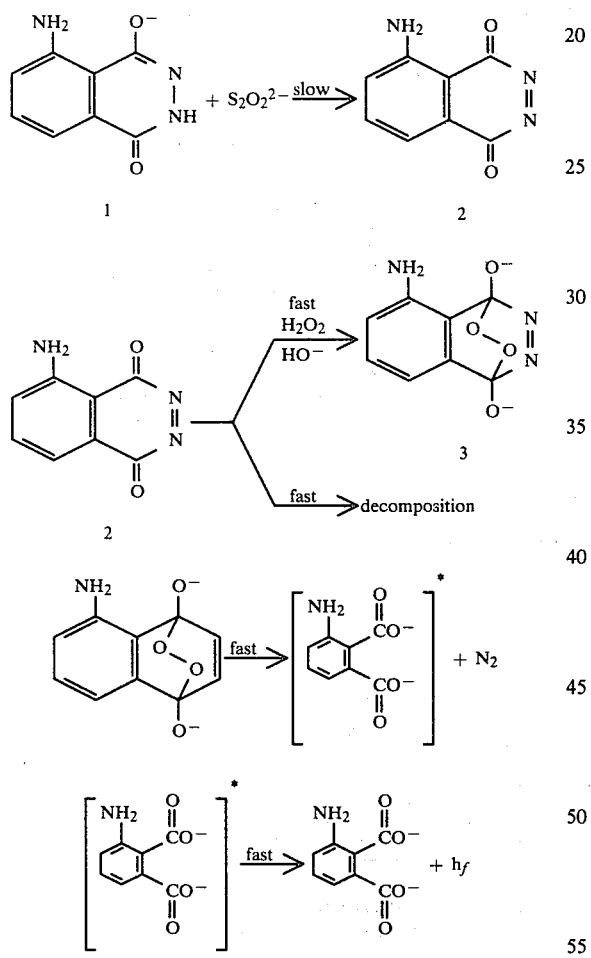

CHART II

Tentative Mechanism for Oxalyl Chloride Chemiluminescence

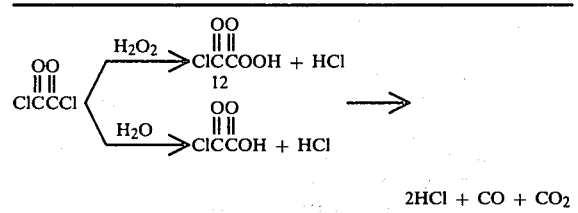

$$2HCl + CO + CO_2$$

CHART II-continued

Tentative Mechanism for Oxalyl Chloride Chemiluminescence

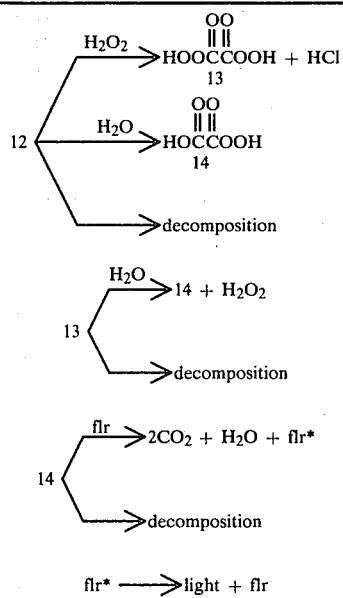

CHART III

Tentative Mechanism for Oxalic Ester Chemiluminescence

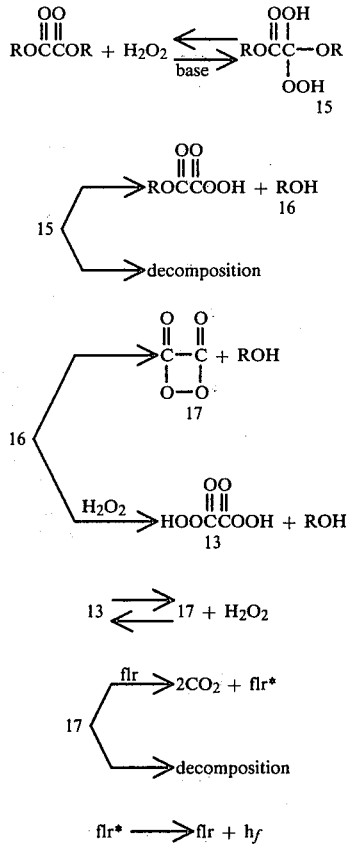

A major difference between the luminol system, which has been used to detect the presence or the quantity of $H_2O_2$, and the oxalate system is the requirement that the oxalates have an additional fluorescer to accept the chemical energy generated in the reaction and then convert that energy to visible light. If the specified fluorescer is absent, the energy generated by the reaction will be dissipated without emitting useful signal. The oxalate system is generally employed in an organic solvent and this requirement also has made its use in CL analytical methods less desirable than other CL materials, which are soluble in an aqueous medium, due to the incompatibility of biological antianalytes to such organic solvents.

The present invention dramatically differs from the prior art utilizing CL for analytical purposes in the way the generated CL energy is employed. The present invention makes use of the CL system as a substrate or reservoir of chemical energy which emits light upon the addition of another compound, i.e. the fluorescer. We have found that by conjugating this fluorescer compound to the anti-analyte of interest it is possible to quantify the analyte's concentration in terms of the amount of emitted light. CL as thus applied becomes competitive as a highly sensitive replacement for radio-immunoassay techniques (RIA).

The comparison of Table 1 shows various analytical systems employing CL and illustrates the manner in which components of different reactions may be used to achieve detection. An analyte may be determined using CL by coupling the detector for the analyte to either:

I. A catalyst for generation of the $H_2O_2$ CL reaction, such as glucose-oxidase, or II. A CL compound which generates CL energy and itself emits light, such as luminol, or III. A fluorescer which accepts chemical energy and emits light, such as a perylene derivative.

In each case, for the purpose of simplicity in this comparison, the analyte is assumed to be surface antigen to Hepatitis B ($HB_SA_g$) in human serum and is determined by a heterogeneous "sandwich" technique. This system is presently widely used with $I^{125}$, a radioactive isotope, as the label or indicator.

TABLE I

COMPARISON OF METHODS FOR USING COMPONENTS OF C.L. REACTION[1]

| | Method I<br>Conjugation of Oxidizeer | Method II<br>Conjugation of Luminol | Method III<br>Conjugation of Fluorescer |
|---|---|---|---|
| Object of of Detection | $H_2O_2$ | luminol | Fluorescer conjugate |
| Label example | glucose oxidase | luminol and derivatives | 3,4,9,10-perylene tetracarboxylic dianhydride |
| Analogous Systems | Williams[2] (1976), Puget[3] (1977) Velan[4] (1978), McCapra[5] (1977) | Hersh[6] (1979), Pratt[7] (1978) Simpson[8] (1979), Schroeder[9] (1979) Olsson[10] (1979) | None |
| Advantages | (1) Enzyme catalyst amplification system for hydrogen peroxide.<br>(2) System can provide a number of readings before destruction.<br>(3) Highest sensitivity for detecting $H_2O_2$. | None | (1) Immunonological reaction separate and distinct from CL production.<br>(2) Highest level of light intensity, 23%.<br>(3) Sample may be retested with additional oxalic ester.<br>(4) Label is stable for coupling and storage.<br>(5) Most desirable functional group may be used for attachment to biological material, minimizing destruction of label, specificity and activity.<br>(6) Fluorescer inexpensive compared with enzyme.<br>(7) Minimal or no instrumentation required for presumptive qualitative analyses. |
| Disadvantages | (1) Many interfering substances also effect luminol reaction and light intensity.<br>(2) Enzyme labeling, reactivity, and kinetics poor.<br>(3) Even with high $H_2O_2$ levels quantum light 1-3% max.<br>(4) Sophisticated instrumentation required<br>(5) Enzyme label expensive. | (1) CL label consumed in reaction, thus sample destroyed.<br>(2) Poor quantum yield of light, less than 1%.<br>(3) Reaction susceptible to other catalysts and quenchers.<br>(4) Sophisticated flow all instruments required. | (1) Oxalate not generally available.<br>(2) Extreme sensitivity of system may cause light emission from traces of foreign fluorescent materials. |

Footnotes to Table 1
[1] No solid phase system incorporating the advantages of a separation of CL, enzyme amplification and immunological chemistry has appeared in literature as described here.
[2] Williams et al. (1976) Evaluation of Peroxyoxalate Chemiluminescence for Determination of Enzyme Generated Peroxide, Anal. Chem., 48, 1003–1006.
[3] Puget et al. (1977) Light Emission Techniques For The Micro-estimation Of Femtogram Levels Of Peroxidase. Anal. Biochem., 79, 447–456.
[4] Velan et al. (1978) Chemiluminescence Immunoassay A New Method For Determination Of Antigens. Immunochemistry, 15, 331–333.
[5] McCapra et al. (1977) Assay Method Utilizing Chemiluminescence. British Patent No. 1,461,877.
[6] Hersh et al. (1979) Luminol-Assisted, Competitive-Binding Immunoassay Of Human Immuno-Globulin G. Anal. Biochem., 93, 267–271.
[7] Pratt et al. (1978) Chemiluminescence-Linked Immunoassay. Journal of Immunological Methods, 21, 179–184.
[8] Simpson et al. (1979) A Stable Chemiluminescent-Labelled Antibody For Immunological Assays. Nature, 279, 646–647.
[9] Schroeder et al. (1979) Immunoassay For Serum Thyroxine Monitored By Chemiluminescence. Journal of Immunological Methods, 25, 275–282.
[10] Olsson et al. (1979) Luminescence Immunoassay (LIA) A Solid Phase Immunoassay Monitored By Chemiluminescence. Journal of Immunological Methods, 25, 127–135.

In order to detect the antigen-antibody reaction the indicator in all cases illustrated in the comparison of Table 1 is taken to be the emission of light from CL. In the "sandwich technique", the following steps are taken: anti-$HB_S$(Goat) is coated to controlled pore glass (CPG) particles in tablet form (solid phase). Patient serum is added to a tube containing a CPG tablet. During incubation the tablet disintegrates. If Hepatitis B Surface Antigen is present in the serum tested, it will combine with the antibody on the glass particles. After incubation, the serum is removed and the glass beads rinsed. A label, as discussed below, conjugated to an anti-body specific for $HB_SAg$ is then added. The labeled antibody combines with the antigen bound to the antibody on the glass particles forming the "sandwich".

The labeled antibody then reacts in a specified manner in the CL system to give light as an indication of antigen presence. This CL assay is a qualitative test for the presence of Hepatitis B Surface Antigen in serum. In general, however, the greater the amount of $HB_SAg$ in a sample, the greater the intensity of emitted light.

The reaction sequence and procedures used in carrying out the Methods illustrated in Table 1 were as follows:

Method I—Enzyme Chemiluminescent Immunoassay

Label: Antibody to Hepatitis B Surface Antigen conjugated with glucose-oxidase (GLO).
Reaction:
(1) Glass.ab.ag+ab.GLO+glucose→$H_2O_2$
(2) Luminol+NaOH+$H_2O_2$ (from reaction 1)→light Procedure: After incubation of the oxidase label to form the "sandwich" as described above, the complex is washed to remove excess label. The washed complex is then incubated for a fixed time with a standard glucose solution to allow the glucose substrate to form $H_2O_2$, the quantity of which is proportional to the original GLO present in the sandwich. An aliquot of the solution is then added to a standard catalyzed alkaline luminol solution with the light emission proportional to the $HB_SAg$ in the original sample.

Method II—Chemiluminescent-labeled Immunoassay

Label: Antibody to Hepatitis B Surface Antigen labeled with luminol.
Reaction: (1) Glass.ab.ag.ab.luminol+$H_2O_2$+hemin→light Procedure: After incubation of the luminol label to form the "sandwich" as described above, the complex is washed to remove excess label. To the washed complex is added a standard hydrogen peroxide alkaline hemin reagent. The light emission is proportional to the $HB_SAg$ in the original sample. It is noteworthy that Hersh et al. (1979) Luminol-Assisted, Competitive-Binding Immuno-Assay Of Human Immumo-Globulin, G. *Anal. Biochem.*, 93 267-271, end their paper describing a similar use of luminol with the following summary:

"The luminol-based chemiluminescent label can be employed as a substitute for radiolabels in immunoassay for serum components at concentrations greater than $10^{-9}$ mol/liter. The main factor limiting the sensitivity of the method is the relatively low overall chemiluminescent efficiency (CE) of the luminol tag. The CE of underivatized luminol is reported to be 1.5% (5). Our luminol-IgG label had a final efficiency of about 0.3%. It is possible that a more efficient means of coupling luminol, if found, would increase sensitivity by a maximum of 600%. The most efficient chemiluminescent system reported to date (not involving enzymes) is the hydrogen peroxide-oxalate ester reaction (6). This reaction has an overall chemiluminescence efficiency of 23%. The use of the oxalate ester as a chemiluminescent label would provide the more substantial gain of 1500% compared to the luminol system."

Thus, while earlier investigators recognized the quantum efficiency of the oxalate system for CL, they, like others, never appreciated the most efficient way to use this oxalate as a source of energy, would be by controlling the "switch" and not the "source" of the energy.

Method III—Chemiluminescent Labeled Light Amplification System

Label: Antibody to Hepatitis B Surface Antigen conjugated to a perylene derivative fluorescer.
Reaction: (1) Glass.ab.ag.ab. perylene+TCPO+$H_2O_2$→light Procedure: After incubation of the perylene label to form the "sandwich" as described above, the complex is washed to remove excess label. The "sandwich" is then washed with tertiary butanol to remove excess buffer salts. Then an excess of bistrichlorophenyl oxalate and hydrogen peroxide in dimethylphthalate are added to cause the fluorescer conjugate to emit light. The light emission is proportional to the $HB_SAg$ in the original sample. The light intensity may be measured qualitatively by eye, or quantitatively by using a photodiode in the same manner that a photomultiplier in proximity to a sodium iodide crystal responds to the photons released by the gamma rays from the $I^{125}$ label.

DISCUSSION OF METHODS I, II AND III

The use of an oxidizer conjugated to an antibody (Method I) is in reality an adaptation of the well-known enzymeimmunoassay systems of Syva Corporation (U.S. Pat. No. 3,817,837) and Organon Co. (U.S. Pat. No. 3,654,090) but here using CL as a light indicator instead of a dye color change. We are not aware of an analogous system incorporating all the solid phase sequences suggested herein. Nonetheless, the detection limit of this method is governed by the ability of the oxidase enzyme conjugate to liberate sufficient $H_2O_2$ as in the above enzyme immunoassays. Some increase in detection level may be achieved by using CL because of the better sensitivity of CL vs. dye color change, this sensitivity does not however approach the detection level of the fluorescer conjugate of Method III.

In Method II a number of analysts have suggested labeling the analyte detector with a CL compound or derivative. This method is inferior to Methods I or III in that the amount of light emitted can never be more than the total energy content of the amount of CL compound conjugated—i.e., luminol or oxalate. A further disadvantage in coupling the CL compound directly to the antibody, for example, is the loss in CL capacity of the conjugate and the continued loss of light as the compound is consumed in the reaction. Finally, the entire loss of the consumed CL compounds before test completion prevents the analyst from repeating or rechecking the sample's CL.

Method III, alternatively referred to as "CLASSIC", the method of the present invention, overcomes the inherent disadvantages of Methods I and II. With "CLASSIC" it is possible to achieve the highest order of activity and specificity of the analyte detector because one can carefully select the preferred attachment site on the biological to be labeled. It is also possible to design the linkage of an efficient and durable fluorescer to conjugate with the biological effectively at this site without damaging the biological. Damage in specificity and activity of biologicals from $I^{125}$ labeling, and damage to enzymes by conjugation is well known and an accepted fact in the preparation of immunodiagnostic reagents. A fluorescent label of preferred utility in CL, by its very structure, must be stable to the oxidizing conditions of the oxalate reaction. This inertness augers well in making fluorescers a particularly efficient form of label for immunochemical analyses.

The various levels of sensitivity and variations in different types of amplification is evaluated in a 1976 review by G. Wisdom, Enzyme-immunoassay, *Clin. Chem.*, 22 1234-1255. These systems provide the amplification for enzyme labels since enzyme catalytic properties allow them to act as amplifiers, and many enzyme molecules can catalyze the formation of more than $10^5$ product molecules per minutes.

To be suitable as a label, an enzyme must meet the several criteria set forth by Wisdom (1976) (supra) which are as follows:

(1) Available cheaply in high purity.
(2) High specific activity.
(3) Stable under assay and storage conditions.
(4) Soluble.
(5) Assay method that is simple, sensitive, rapid, and cheap.
(6) Absent from biological fluids.
(7) Substrate, inhibitors, and disturbing factors, absent from biological fluids.
(8) Capable of retaining activity while undergoing appropriate linkage reactions.
(9) Capable of inhibition or reactivation when antibody binds to the enzyme-hapten conjugate.
(10) Assay conditions compatible with hapten-antibody binding.

These specifications are easily met by fluorescers which may be readily incorporated as labels capable of accepting the chemical energy from the oxalate "substrate". In addition, as has been shown by Rauhut, certain selected fluorescer structures are capable of catalyzing the peroxyoxalate reaction products, thus providing the type of amplification available with enzymes. A rationale for this catalysis has been advanced by Schuster (1979) *Accts. of Chem. Res.*, 12, 366.

The CL system of the present invention, "CLASSIC", also has certain advantages over fluorescent antibody techniques which make use of the ability of a fluorescent tag to emit light of a particular wave length when excited by radiant energy of a lower wave length. A number of clinical analyses which utilize fluorescent "probes" or tags have been described in a recent review by Soini (1979) Fluoroimmunoassay: Present Status and Key Problems. *Clin. Chemistry*, 25, 353-361. In general, the detection level, or sensitivity, of fluoroimmunoassay techniques is greater than enzyme immunoassay techniques and approaches the capability of radioimmunoassay systems.

The use of fluorescent probes to replace radioactive isotopes is hindered by the decreased sensitivity obtained with fluorescence. This is due, to a great extent, to the sample's or serum's own fluorescence. The intensity of this background is affected by many fluorescing compounds, such as protein which may be present in the sample, and which also increase scattering caused by the specimen.

Fluorescence methods are now extensively applied in immunology, mainly in fluorescence microscopy, for studying various types of tissues, cells, bacteria, viruses and so on. A number of fluorescent materials and procedures for coupling them to the above biologicals and haptens is well developed.

To take advantage of the full scope of this invention, special high intensity fluorescent molecules are required. These must be capable of biological coupling with protein, polysaccharide and hapten substances, especially immunoglobulins—i.e., $I_gG$ —and antigens without disturbing the specificity or activity of these biological materials.

Bellin (1968) Photophysical and Photochemical Effects of Dye Binding. *Photochem. and Photobiol.*, 8 383-342 and Porro et al. (1963 and 1965) Fluorescence And Absorption Spectra of Biological Stains. *Stain Technology*, Vol. 38, and Fluorescence And Absorption Spectra Of Biological Dyes (II). *Stain Technology*, Vol. 40, No. 3, 173-175, respectively, have shown that there is a reduction in efficiency in the light output of fluorescers as a result of bonding or conjugation to proteins as compared to the output of these fluorescers in free solution. Our work has shown a similar loss in output, however, the energy efficiency of the oxalate system compensates for this loss. While this loss in light output effects all other known applications of conjugated fluorescers, the analytical method of the present invention requires a conjugate only during the biological antibody/antigen formation phase of the analysis. Procedures are well known for preparing a conjugate of a fluorescer in a manner which permits the conjugate to be subsequently separated at will by changing the pH, or other parameter, of the conjugate solution. It should also be noted that the immunochemical reaction of CLASSIC, Method III, may be carried out in the environment best suited for the optimum detection of the analyte of interest. After the label has been identified with the analyte one may then separate the label, the fluorescer, from the conjugate which allows the fluorescer to enter the solvent phase of the CL system to yield the maximum light efficiency.

In general, it is desirable to provide the high quantum efficiency of fluorescing aromatic and substituted hydrocarbons, heterocyclic compounds, dyestuffs, and metal chelates with the ease of conjugation to the biological now available for microscopy reagents. We have found that we can couple the fluorescer using known procedures currently accepted for use with the fluorescent conjugates such as set forth in Soini (1979) Supra, the teachings of which are incorporated herein by reference.

The following Tables 2 and 3 from Soini (1979) supra, set forth data on various fluorescent materials some of which can be advantageously employed as labels.

TABLE 2

Published Data on the Properties of Fluorochromes Used for Various Purposes, Including Decay Times ($\tau$), Quantum Yields (Q), Excitation and Emission Wavelengths, Absorbances ($\epsilon$), and the Sensitivities of Fluorescence to Polarity Changes in the Environment[a]

| Fluorochrome | $\tau$, ns | $Q_1$ | $Q_b$ | Exc. max., nm | Em. max., nm | Mol. absorp. | Sensitivity of fluorescence to changes | Reference(s) |
|---|---|---|---|---|---|---|---|---|
| FITC | 4.5 | | 0.85 | 492 | 518 | 72 000 | stable | 50, 51, 52, 53 |
| TRITC | | | | | 518 | 48 000 | stable | 55-60 |
| RBITC | 3 | | 0.7 | 550 | 585 | 12 300 | stable | 55, 57, 58 |
| RB200SC | 1 | | 0.04 | 530, 565 | 595, 710 | | stable | 48, 49, 55 |
| DNS—Cl | 14 | 0.2 | 0.3 | 340 | 520–480 | 3 400 | sensitive | 31, 32, 42, 47 |
| Fluoram | 7 | 0.00 | 0.1 | 394 | 475 | 6 300 | sensitive | 46, 65 |

TABLE 2-continued

Published Data on the Properties of Fluorochromes Used for Various Purposes, Including Decay Times (τ), Quantum Yields (Q), Excitation and Emission Wavelengths, Absorbances (ε), and the Sensitivities of Fluorescence to Polarity Changes in the Environment[a]

| Fluorochrome | τ, ns | $Q_l$ | $Q_b$ | Exc. max., nm | Em. max., nm | Mol. absorp. | Sensitivity of fluorescence to changes | Reference(s) |
|---|---|---|---|---|---|---|---|---|
| MDPF | 0 | | 0.1 | 390 | 480 | 6 400 | not | 61–64 |
| NBD—Cl | | | | 468 | 530 | 12 900 | sensitive | 44, 45 |
| ANS (ANM) | 16 | 0.0 | 0.9 | 385 | 471 | | sensitive | 41, 29 |
| NPM (PBA) | 100 | 0.0 | | 340 | 392, 375 | | sensitive | 37, 38, 39, 40 |
| DACM | 5 | 0.0 | 0.5 | 383–398 | 480–482 | 24 200 | sensitive | 29, 33, 34, 35 |
| BIPM | 1 | 0.0 | 0.5–0.8 | 310–315 | 360 | 28 000 | sensitive | 29, 33 |
| anthracene-ITC | 29 | | 0.6 | 357 | 460 | 3 040 | not | 48 |
| FAM | 20 | | 0.2 | 362 | 462 | | | 29, 36 |

List of abbreviations for Tables 1 and 2:
ANS, 1-anilino-8-naphthalenesulphonic acid;
ANSC, 1-anilino-8-naphthalenesulphonyl-chloride;
BIPM, N—(p-2-benzimidazolyl-phenyl)-maleimide;
DACM, N—(7-dimethylamino-4-methyl-2-oxy-3-chromenyl)-maleidime;
DNS—Cl, dansylchloride, dimethylaminonaphthalene-5-sulphonylchloride;
FAM, fluoroanthylmaleimide;
FITC, fluorescein-isothiocyanate;
Fluoram, fluorescamine, 4-phenylspiro-(furan-2(3H)-1-phthalan)-3,3-dione;
MDPF, 2-methoxy-2,4-diphenyl-3(2H)-furanone;
NBD—Cl, 7-chloro-4-nitrobenzo-2-oxa-1,3-diazole;
NPM, N—(3-pyrene)-maleimide;
PBA, pyrenebutyric acid;
RBITC, rhodamine-B200-isothiocyanate;
RB-200-SC, lissamine-rhodamine-B200-sulphonylchloride;
TNS, toluidinonaphthalenesulphonic acid;
TRITC, tetramethylrhodamine-isothiocyanate.

[a]($Q_l$ = quantum yield of free fluorochrome, $Q_b$ = quantum yield of fluorochrome bound to protein).

TABLE 3

Fluorescence Maxima and Detection Limits of Some Probe Conjugates Based on Measurements by the Authors[a]

| Probe | Binding type | Fluorescence max. (nm) Excitation | Fluorescence max. (nm) Emission | Detection limit In a buffer | Detection limit In serum (1/10) | Remarks |
|---|---|---|---|---|---|---|
| FITC—BSA | covalent | 491 | 517 | 30 ng/mL | 1000 ng/mL | Interference by scattering |
| —hIgG | covalent | 491 | 517 | 40 ng/mL | 1400 ng/mL | Interference by scattering |
| —thyroxine | covalent | 490 | 515 | 1 pmol/mL | 35 pM/mL | Interference by scattering |
| RBITC—BSA | covalent | 552 | 572 | 100 ng/mL | 430 ng/mL | Interference by scattering |
| DNS—BSA | covalent | 360 | 514 | 100 ng/mL | 7000 ng/mL | Interference by serum fluorescence |
| —hIgG | covalent | 360 | 514 | | | |
| —thyroxine | covalent | 330 | 480 | 30 nmol/mL? | 2100 nmol/mL | Interference by serum fluorescence |
| —cys-digoxin | covalent | 358 | 533 | 140 pmol/mL | 98 nmol/mL | Interference by serum fluorescence |
| Fluoram—BSA | covalent | 393 | 465 | 1500 ng/mL | 32000 ng/mL | Interference by serum fluorescence |
| —hIgG | covalent | 393 | 465 | | | |
| —thyroxine | covalent | 395 | 480 | 25 pmol/mL | 535 pmol/mL | Interference by scattering fluorescence |
| NPM—BSA | covalent | 335 | 392 | 100 ng/mL | 1500 ng/mL | Interference by scattering and fluorescence |
| —IgG | covalent | 340 | 392 | 2000 ng/mL | | [b] |
| ANS—BSA | noncovalent | 385 | 470 | | | |
| ANSC—BSA | covalent | 380 | 470 | 10000 ng/mL | | [c] |
| TNS—BSA | noncovalent | 322, 360 | 429 | | | [d] |
| NBD—BSA | covalent | 468 | 526 | 4000 ng/mL | 240 μg/mL | [e] |

[a]Measurement results have been obtained with some commonly used probes as conjugates of bovine serum albumin, IgG, thyroxine, and digoxin. Conjugation was by common methods described in the literature (47, 37, 46, 44). No attempt was made to optimize measurement in any way; this was done directly at emission maxima for bandwidths of 10 nm. No cut-off filters were used. It would probably have been possible to reduce the detection limits of some probes considerably by altering the slit-values and by adjusting the measurement wavelengths, and by using suitable cut-off filters (The emission of fluorescein for example is usually measured at 540 nm, although the emission maximum occurs at 515 nm.) The fluorescence and detection limits for different probe-conjugates were measured with a Perkin-Elmer fluorescence spectrometer, Model MPF-2A. The detection limits were measured in the regions of excitation and emission maxima, and the values compared with the background fluorescence values of diluted serum at the same wavelengths and with the same instrument sensitivity.
[b]No reaction in IgG, SH-groups.
[c]Serum background, may bind to different proteins.
[d]Interference by protein fluorescence.
[e]Interference by serum fluorescence, own fluorescence weak.
BSA, bovine serum albumin; hIgG, human immunoglobulin G.

Typical of fluorescers which provide derivatives to which the biological may be coupled are those set forth by Pringsheim (1946) Luminescence Of Liquids And Solids And Its Practical Applications. *Interscience Publishers, Inc.*, New York, NY.

In addition to the organic fluorescers listed by Pringsheim, a number of metal organic materials have been suggested for laser fluorescent assay systems: Ruthenium (II-tri(bibyridyl) complex has been identified by Curtis et al. (1977), Chemiluminescence; A New Method For Detecting Fluorescent Compounds Separated By Thin Layer Chromatography, *J. Chromatography,* 134, 343–350 for CL applications; Metal Complexes by Sherman (1978), Analytical Applications Of Peroxyoxalate Chemiluminescence, *Analytical Chem. Acta,* 97, 21–27 and Soini (1979) supra. Weider U.S. Pat. No. 4,058,732 disclosed and suggested their immunofluorescent application. It is also well known, Van Uitert (1960), Factors Influencing The Luminescent Emission States Of The Rare Earths. *J. Electrochem. Soc.,* 107, 803, that small additions of the rare earth and/or transition metals function as promotors, activators or coactivators in inorganic and organic phosphors. Thus, it is not unexpected that trace impurities will behave in a similar manner in other organic and metallo-orgnic systems and have a profound effect on the quantum efficiency of the fluorescer.

The discussion has thus far centered around the novel analytical use of a fluorescer-biological conjugate activated by the chemical energy from a peroxyoxalate CL system. The preferred peroxyoxalate system is advantageous for CL because of its quantum efficiency and because there is minimal background light in the absence of a fluorescer conjugate. This system is particularly "noise free" when certain intensity control additives are eliminated, such as are disclosed by Bollyky (1972) *Chemiluminescent Additives* U.S. Pat. No. 3,704,231. A system for analytical purposes need only provide light of high intensity for a short period, that is, for example, under about 30 minutes.

While peroxyoxalates which are "noise free", or non-fluorescent are preferred, other naturally self-fluorescent oxalate esters or CL compounds are also useful with the proper selection of a barrier filter and use of a fluorescer of longer wavelength. Such esters include 2-napthol-3,6,8-trisulfonic acid, 2-carboxyphenyl, 2-carboxy-6-hydroxyphenol, 1,4-dihydroxy-9, 10 diphenylanthracene, 2-napthol, as well as aqueous CL materials such as luminol, lophine, pyrogallol, luciferin, and related compounds.

Other systems besides those mentioned are also capable of activating a CL fluorescer-conjugate.

These include: (1) Ozone, which has been shown by Randhawa (1967), Ozonesonde For Rocket Flight, *Nature,* 213, 53 to activate Rhodamine-B. (2) Keszthelyi et al. (1969), Electrogenerated Chemiluminescence: Determination Of Absolute Luminescence Efficiency, etc., *Analytical Chem.,* 47, 249–256, has demonstrated electro-generated CL in 9,10-diphenylanthracene, thianthrene, and rubrene, with some systems. Thus, Ozone or electro-generated CL in the presence of the fluorescer-conjugate can provide other useful energy sources for the CL fluorescer systems of the present invention. In addition, other known energy sources such as have been found useful in applications involving the distortion of various polymers by mechanical energy and other similar systems which yield free radicals are also useful in the present invention.

It should be understood that many analytical system variations are possible, but all have in common the use of a labelled immunological specie specific to the analyte. The analyst has the latitude in selecting a procedure which provides the detection level required from a minimum amount of sample and which uses the least expensive and most reliable instrument. The detection level required is a function of the antigen, antibody or hapten concentration in the analyte and its clinical significance.

For clinically significant dosage testing—i.e. Digoxin, standard curves are obtained from known samples analyzed together with the unknown and run under carefully controlled duplicate analyses on highly calibrated instruments. While a presumative test for an immunoglobin requires a much lower level of sophistication, it is highly advantageous for a single analytical system to be able to cover this analytical spectrum.

The sophisticated analytical requirements may be met by using a Centrifugal Fast Analyzer such as that made by Electro-Nucleonics, Inc. Burtis et al. (1975). Development Of a Multipurpose Optical System For Use With A Centrifugal Fast Analyzer. *Clinical Chemistry,* 21 1225–1232. For the $N^{th}$ nations lacking the ability or need for such sophistication, or for presumptive testing at the physician's office or clinic, no instrument is required. The "CLASSIC" system of the present invention delivers sufficient intensity to the labeled biological to enable the clinician to make a simple go-no-go determination by "eye-balling".

The clinician may also modify the role of the labeled specie used in carrying out the analyses. While solid phase techniques have been used as examples to illustrate the advantages of the present invention, it should be recognized that homogeneous and heterogeneous assays also will benefit from the use of the "CLASSIC" system. Acceptable alternative variations in test procedure include:

(1) Competitive binding of labeled antigen.
(2) Competitive binding of labeled antibody.
(3) Quenching analyses.
(4) Immunoprecipitant reactions.
(5) Ion exchange methods.
(6) Ion exclusion methods.

DESCRIPTION OF THE PREFERRED EMBODIMENTS

The major components for the preferred "light-switch" or "light indicator" of the present invention are similar to those disclosed in U.S. Pat. No. 3,597,362. They include an oxalic ester, a hydroperoxide, a fluorescer (or fluorescent compound) and a diluent. Furthermore, in order to generate maximum intensity of light, the employment of an additional catalytic accelerator is sometimes necessary. The choice and the concentration and other parameters of a suitable catalytic accelerator is also described in U.S. Pat. No. 3,704,231.

The present invention differs from the teaching of U.S. Pat. No. 3,597,362 in that the fluorescent compound (or fluorescer) employed in this invention is covalently bonded to a biological material, such as immunoglobulin, enzymes, proteins, bacteria, and so on; or to an organic material, such as haptens or polymers; or to an inorganic material, such as glass, silica, ceramic, or the like. The organic and inorganic materials with which a suitable fluorescer may be incorporated can be in the form of particles, crystals, tubes, rods, plates, blocks and the like, or in solution. The fluorescent compound, or fluorescer, incorporated with the above mentioned substances can then be utilized as a label in place of radioactive materials or as an indicator in place of color dye, for use in various well-known assays.

Especially suitable fluorescent compounds, or fluorescers for use in the present invention are those which have a spectral emission falling between 350 millimicrons and 1,000 millimicrons. The structure of the fluorescent compounds or fluorescers useful in the present invention must possess one or more functional groups capable of reacting with those materials to be coupled to it. Examples of preferred functional groups are: alkylamino-, arylamino-, isocyano-, cyano-, isothiocyano-, thiocyano-, carboxy-, hydroxy-, mercapto-, phenol-, imidiazole-, aldehyde-, epoxy-, thionyl halide-, sulfonyl halide-, nitrobenzoyl halide-, carbonyl halide-, triazo-, succinimido-, anhydride-, haloacetate-, hydrazino-, dihalo triazinyl-. Typical examples of suitable fluorescer derivatives are: 3,4,9,10 perylene tetracarboxylic dianhydridge, amino-chrysene, fluorescein isothiocyanate, teteramethylrhodamine isothiocyanate, amino-pyrene, amino-anthracene, and similar compounds as will be familiar to those skilled in the art.

It has been observed that on binding a fluorescent compound, or fluorescer, to a solid material, the wavelength of emission of the incorporated fluorescer shifts to either a longer or a shorter wavelength depending on the specific fluorescer microenvironment employed.

We have also found that the length of "space arm" the ligand between the fluorescers and the material bonded to it, effects the emission wavelength of the bonded fluorescer.

The exact concentration of fluorescer derivative incorporated is not critical providing that the immunological or enzymatically active fluorescent incorporated product has the desired activity, and that the intensity of light thus produced is visible, with or without the help of instruments, and may be differentiated from the background.

The intensity of the light generated by the coupled fluorescer depends upon the structure of the fluorescer, the type of linkage between the fluorescer and the bonded materials, and the available functional groups of the anchored substance. In general, the intensity of the light produced by a fluorescer is not as great after coupling as it is when in free solution. It is also important that the fluorescer conjugate be stable in the presence of the chemiluminescent reaction.

U.S. Pat. No. 4,238,195, which issued on Dec. 9, 1980 describes an assay method employing a fluorescer as a label and claims the improvement comprising measuring said fluorescent label by chemically exciting said label to cause the same to emit light and then measuring the light emitted. This reference sets out a number of assay methods in which the claimed invention may appropriately be employed.

The teachings of said U.S. Pat. No. 4,238,195 are hereby incorporated by reference in the present application.

The present invention provides for an improved method for carrying out an assay employing an encapsulated fluorescer or quencher/poison label wherein the encapsulated fluorescer label is to be excited either chemically or by other non-radiant energy means. It has been found that higher quantum efficiency of fluorescer and light output may be obtained by encapsulating the fluorescers. The microcapsule is then conjugated as a label to the biological.

After completion of the biological analysis which carries the microcapsule containing the fluorescer label through the aquous phases, the microcapsule is disrupted releasing the fluorescer in an unbound state. This improvement offers the following advantages over previous art:

(1) More fluorescer label is available without effecting the biological activity of the conjugate.

(2) The fluorescer in solution is more efficient than bound fluorescer.

(3) There is no requirement for any reactive group on the fluorescer.

(4) Excess fluorescer is more readily separated from the biological after incorporation.

(5) The ability to select either hyrophillic or hydrophobic fluorescer.

(6) Allows one to select the most efficient fluorescer catalyst/or poison for the high energy intermediate.

(7) Allows one to minimize the non-specific absorption of the fluorescer probe to other proteins which increases the overall sensitivity of the analysis.

While the use of fluorescer labels has been previouslly described and the advantages of the use of excited or non-radiative energy to enhance the fluorescence signal from these fluorescers when conjugated to a biological for use as immunological assay's probe has been noted, the advantage of the chemiluminescence assay's sensitivity is often limited by non-specific binding reactions and the inherently limited choice in selecting the quantity of the most advantageous fluorescer molecule for the specific assay to be undertaken.

It has now been discovered that by utilizing recently developed encapsulation techniques we can eliminate the restrictions imposed by direct conjugation of the fluorescer label to the biological.

Encapsulation means any method whereby a carrier such as a liposome or polymer for a fluorescer or quencher/poison incorporates such fluorescer or quencher/poison in such a manner that it may be attached to a biological specie specific to an analyte of interest and later released free into solution.

Many encapsulation processes are known to the art, which will allow one to prepare suitable encapsulated fluorescers as the mechanism as now understood.

In order to function in any efficient immunoassay the encapsulating system should possess the following properties:

(1) Colloidal size sufficient small to permit free suspension and not inhibit the movement and immunological binding of the labelled species, uniform size is essential.

(2) Internal volume of the microcapsule should be as large as possible, i.e. that is to say the microcapsule should have a minimal wall thickness for containment. Alternatively the microcapsule should have a maximum wall thickness for embedding the fluorescer, in the event such a technique is employed.

(3) The microcapsule should have one or more reactive groups to enable its conjugation with the biological.

(4) The microcapsule should be stable in the environment of the biological assay.

(5) The membrane of the microcapsule should be easily disrupted to allow the fluorescer to escape to solution, but with minimal detriment to the chemiluminescent signal to be generated by the fluorescer.

(6) The enclosed fluorescer should be contained as a liquid or solid with minimal leakage from the microcapsule.

(7) The microcapsule should be stable and provide long shelf life with minimal storage and environmental requirements.

(8) The microcapsule may possess positive, negative or neutral charge on its surface.

(9) The microcapsule should be easily and economically produced.

The improved method of the present invention allows for the utilization in any conventional assy, such as those previously described, or as set forth in U.S. Pat. No. 4,238,195, referred to above, an encapsulated fluorescer as the label, so long as the encapsulating technique used to form the microcapsule or sac containing the fluorescer material permits the inclusion of a large concentration of fluorescer, has appropriate binding sites on the surface of the microcapsule or sac to allowing for conjugation to a immunological specie specific to the analyte of interest and the encapsulating material is readily disruptable to free the contained fluorescer which may subsequently be excited to emit light.

Liposomes as small as 250A° have been prepared by techniques described by Papahadjopoulos (1978), Korn (1973), Huang (1969) and Bangham (1976).

The incorporation of fluorescers as markers for cell surface studies when excited by u.v. light has been demonstrated by Weinstein (1977).

Torchilin (1979) and Heath (1980) have successfully incorporated a conjugatable binding site to the liposome bilayer.

This work provides us with the ability to place bound and unbound fluorescent probes in microcapsules or sacs. The sacs may be filled with far more of the fluorescer of choice than could heretofore effectively be conjugated directly to the biological be be used for the assay probe.

The fluorescer to be incorporated into the microcapsule or sac of the present invention may also be selected to optimize the catalysis of the high energy intermediate, and also to optimize the emission spectra from the probe. As a result one can achieve improved signal/noise output of the system by at least 25 times and vastly broadened the category of practical fluorescers, which may be utilized in carrying out any fluorescer labelled assay.

The preferred fluorescers to be incorporated into the microcapsule of the present invention include 5,12-dihydro quinoxalo(2,3,6) phenazine magnesium and zinc metalo porphyrins, neutral red, magdalla red, acridine red, acridine orange, dianisyl ethynyl tetracene phenizine, rhodamine, 3,4,9,10 perylene tetracarboxylic dianhydride, and derivatives thereof or similar materials which meet the requirements stated above.

The following examples are given to illustrate the various ways the fluorescer may be attached to another moiety by covalently bonding using an inorganic support for convenience, which is in no way intended to limit the scope of the invention described herein.

EXAMPLES I-V

In each of the Examples I-V the linkage attached to a controlled pore glass surface was synthesized to imitate the representative chemically active sites on a typical protein or biological conjugate. For example, amino-, carboxyl-, mercapto-, or hydroxyl-groups are representative of attachment sites.

A glass support is used so that the activity and specificity of the functional group is easily controlled, and to immobilize the fluorescer so that it may be readily separated from the free or unbound fluorescent compound in order that the fluorescent spectra may easily be recognized as distinct from the oxalate CL reagent.

The results of visual observation as to the color of the fluorescent glass, and color and intensity of emitted light for 1-aminopyrene covalently bonded to porous glass (CPG) (500 A pore size) fluorescer with various different linkages are set forth in the attached Table 4.

The methodology employed for preparing each fluorescer/glass sample was as follows:

EXAMPLE I

Ten grams of porous glass of 500 (Å) (angstrom pore size) was treated with 100 ml 15% gamma-aminopropyltrimethoxysilane in toluene and refluxed for at least 16 hours, then removed. The unbound silane was thoroughly washed with methanol, filtered and the glass air dried before use. Approximately 25 milligrams 1-aminopyrene was dissolved in dioxane (20 millimeter). To this solution about 153 milligrams of succinic anhydride was added. After two hours, 10 millimeter of 5 m mole N,N-dicyclohexyl-carbodiimide dioxane solution was added. 500 mg of this gamma-aminopolytrimethoxysilane treated glass (from here on, aminopropyl-glass) as prepared above was added to dioxane solution. The slurry was then stirred for one hour and let stand overnight at room temperature. Continuous stirring is preferable. The excess pyrenedioxane solution was decanted and the glass washed exhaustively with dioxane, methanol and acetone (15 ml of each wash and three times for each solvent). The wet pyrene coupled glass was filtered and allowed to air dry.

EXAMPLE II 500 mg of the aminopropyl-glass prepared as stated in Example I was added to 25 ml of 10% thiophosgene in chloroform and the slurry was refluxed for 4 hours. The chloroform was decanted and then washed with chloroform, methanol, acetone (25 ml of each wash and three times for each solvent). The slurry was filtered and air dried. 30 milligrams of 1-aminopyrene was dissolved in 15 ml dioxane. To this solution, the dry isocyanato-glass was added and stirred for one hour and then allowed to stand at room temperature overnight. After the reaction was complete, aminopyrene dioxane solution was decanted and the pyrene coupled glass was washed in the same manner as stated in Example I.

EXAMPLE III 500 mg of aminopropyl-glass, prepared as stated in Example I, was added to 10 ml of dioxane dissolved with 50 mg succinic anhydride. The slurry was allowed to stand overnight at room temperature preferably with continous stirring. After the reaction was complete, the aminopropyl-glass, being converted to carboxy-glass, was washed in the same manner as stated in Example I. Approximately 23 mg 1-aminopyrene was dissolved in 1 ml of dioxane. To this solution, 58 mg of N-acetyhomocystein was dissolved. The solution was then kept 4 hours at room temperature. 50 mg of N,N-dicyclohexyl-carbodiimide was then added to it. At the same time, the prepared and dried carboxyl-glass was added to the solution for coupling. The reaction was allowed to stand at room temperature for 24 hours. Pyrene coupled glass was then washed and dried in the same manner as stated before.

EXAMPLE IV 4 grams of aminopropyl-glass prepared from Example I was added to 10% p-nitrobenzoyl chloride with 1 ml of triethylamine in 50 ml chloroform solution. The slurry was stirred and refluxed for at least 8 hours. The resulting acylated glass was thoroughly washed with chloroform and let air dry. 0.1 M of sodium dithionite (30 ml) was prepared and the acylated glass was added. The temperature was then raised to 40° C. The reaction was completed in one hour. The glass was washed thoroughly with warm water. The arylamino-glass thus prepared was ready to diazotize. 1 gm of arylamino-glass was added to 20 ml aqueous solution of 350 mg sodium nitrite and 0.2 ml 1 N hydrochloric acid. The temperature was brought down to 4° C. using an ice bath. The reaction was allowed to continue for one hour. The acid solution was then decanted, the glass was thoroughly washed and the pH was adjusted to above 8.0. The filtered glass was then added to 10 ml of 20 mg aminopyrene dioxane solution. Reaction was complete in 8 hours at room temperature. The pyrene coupled glass was then washed in the same manner as in Example I.

EXAMPLE V

One gram of 500 (Å) pore size porous glass treated with 10 ml of 15% gamma-glycidoxypropyltrimethoxysilane in toluene and refluxed for at least 16 hours, then washed the glass with acetone thoroughly and air dried. To 30 ml aqueous solution containing 1.5 mg/ml of m-sodium periodate, the silane treated glass (epoxy-glass) was added. The reaction was allowed to go on for 2 hours. Then the glass was washed with water thoroughly. 25 mg of 1-aminopyrene was dissolved in 30 ml dioxane. To this solution, the filtered wet cake glass was added. The slurry was stirred for one hour and then let stand overnight at room temperature. Then pyrene coupled glass was washed in the same manner as stated in Example I.

dioxane solution containing 200 mg of N,N-dicyclohexyl carbodiimide. The glass was stirred for 24 hours and then washed with dioxane and methanol. 20 ml of 200 mg hexamethylene diamine aqueous solution was prepared and cooled beforehand. The activated carboxy-glass was added to the cooled solution and stirred for five hours, then allowed to stand for 24 hours at 4° C. The glass was then washed thoroughly with water, methanol and dioxane. 20 ml dioxane containing 50 mg succinic anhydride was then added to the glass. This reaction was completed in 24 hours. The glass was subsequently washed thoroughly with methanol, 25 mg 1-aminopyrene was dissolved in 30 ml dioxane. To this solution 5 m mole N,N-dicylohexylcarbodiimide was added and dissolved prior to adding the prepared glass. The slurry was stirred for one hour and then let stand overnight at room temperature. After 24 hours reaction, pyrene coated glass was then washed in the same manner as in Example I.

Pyrene coated glass with a short "space arm" of about 10 (Å) in length was prepared as stated in Example I, as the control. The results of these two glasses is set forth in attached Table 5.

TABLE 5

EXAMPLE VI
Effect of "Space Arm" Length Between Glass Surface
and the Fluorescer on Chemiluminescent Characteristics

| Approximate Length of "Space Arm" | Color of Light | Intensity Observed* |
|---|---|---|
| (Example I) Control 10(Å) | bluish-green | M |
| Example VI 20 (Å) | green | W-M |

*M = medium; W = weak

EXAMPLES VII–IX

TABLE 4

EXAMPLES I-V
Effect of Different Linkages

| Example No. | Type of Linkage | Structure | Color of Fluorescent Glass | Color the Light** Emits on Glass Particle | Intensity* Observed |
|---|---|---|---|---|---|
| I | Amido | Flr—N(H)—C(=O)—(CPG) | blue-green | bluish green | M |
| II | Thiourea | Flr—N(H)—C(=S)—N(H)—(CPG) | blue-green | bluish green | M |
| III | Thio-ester | Flr—S—C(=O)—(CPG) | grayish green | bluish green | W-M |
| IV | Diazo | Flr—N=N—(CPG) | red-brown | red-brown | VW |
| V | Amide | Flr—N(H)—C(H)—(CPG) | as CPG | blue | M |

*M = medium; W = weak; VW = very weak
**After addition of oxalate ester and hydrogen peroxide

EXAMPLE VI

Different lengths of "space arm" for binding of the fluorescer were used to study the effect on the chemiluminescence quality of the resultant bonded fluorescer.

A long "space arm" of about 20 (Å) in length stretching out from a controlled glass pore surface was prepared as follows: 500 mg of carboxy-glass prepared as stated in Example III was activated by adding a 20 ml Porous glass having various pore sizes were coated with 1-aminopyrene to show the effect of pore size on the chemiluminescence. Three different porous glasses having 170 (Å) (angstrom), 500 (Å) and 3000 (Å) pore size, respectively, were coatd with 1-aminopyrene in the same manner as stated in Example I. The effect on the chemiluminescence is set forth in attached Table 6.

TABLE 6
EXAMPLES VII-IX
Effect Of Pore Size On Chemiluminescence

| Example No. | Pore Size (in angstrom) | Surface Area (in $M^2$/gm) | Color of Fluorescent Glass Before Coating | Color of Fluorescent Glass After Coating | Color of Light Emitted | Intensity Observed |
|---|---|---|---|---|---|---|
| VII | 170 | 110 | clear | green | yellowish green | M |
| VIII | 500 | 50 | lt. blue | lt. blue | bluish green | W-M |
| IX | 3000 | 10 | white | white | blue | W |

EXAMPLES X-XV

Several different fluorescers were coated on porous glass to study the effect of structure on color emission. 1-aminopyrene and 2-amino-anthracene were coated on the porous glass (500 Å) in the same manner as described in Example I.

20 mg of 3,4,9,10-perylenetetracarboxylic dianhydride was added to 25 ml of dioxane, to this solution 25 mg of aminopropyl-glass was added and stirred for one hour before allowing to stand for another 6 hours at room temperature. The glass was then washed thoroughly with methanol or acetone, then filtered and air dried.

500 mg of aminopropyl-glass was added to 30 ml dioxane containing 50 mg succinic anhydride and stirred for one hour before being allowed to stand overnight at room temperature. The glass was then washed thoroughly with acetone, filtered and air dried. One part of 250 mg of such glass (carboxyl-glass) was added to 25 ml 0.01 M potassium phosphate of pH=7.6 solution containing 20 mg of isothiocyanate fluorescein. Another part of 250 mg of carboxyl-glass was added to acetone/dioxane (50/50 by volume) solution containing 20 mg of 3-amino-phthalhydrazide. The two glass slurries were stirred for one hour and then allowed to stand at room temperature overnight. After the reaction was completed, the glass was washed with deionized water and acetone, respectively. Finally, they both were washed with acetone, then filtered and air dried.

300 mg of aminopropyl-glass prepared as shown Example I was added to 50 ml 0.01 M potassium phosphate of pH=7.6 solution containing 25 mg of O-phthalic-dicarboxaldehyde. The glass slurry was stirred for one hour, then allowed to stand at room temperature for another 24 hours. The glass was then washed thoroughly with deionized water, acetone, then filtered and air dried.

The attached Table 7 sets forth in the observed chemiluminescence characteristics of different fluorescers bonded to porous glass in an oxalate ester/peroxide system.

TABLE 7
EXAMPLES X-XV
Comparison of Chemiluminescence of Different Fluorescers Free and Covalently Attached to Porous Glass of 500(A) Pore Size

| Fluorescer | Example No. | Color of Fluorescent Glass | Color of Light - Bonded Fluorescer | Intensity of Light Observed | Color of Light - Free Fluorescer | Fluorescence U.V. Light |
|---|---|---|---|---|---|---|
| 1-aminopyrene | X | blue green | bluish green | M | green | negative |
| 2-amino-antracene | XI | lt. brown | violet | M | blue-violet | negative |
| 3,4,9,10-perylene tetra-carboxylic dianhydride | XII | orange red | orange-red | M | none | orange |
| Fluorescein isothiocyanate | XIII | yellow | green | M | green | yellow |
| 3-amino-phthal hydrazide (luminol) | XIV | lt. blue | bright blue | M | blue | blue |
| 0-phthalicdi-carboxaldehyde | XV | yellowish-brown | greenish-yellow | W-M | none | negative |

EXAMPLE XVI

Aminopyrene conjugate with antibody to Hepatitis B Surface Antigen coated on porous glass.

30 mg commercially available antibody to Hepatitis B Surface Antigen coated porous glass was added to 5 ml of 0.01 m potassium phosphate of pH=7.6. 24 mg of 1-aminopyrene was dissolved in 2 ml dioxane. To this solution 45 mg of succinic anhydride was added and mixed for two hours. Approximately 95 mg of N,N-dicyclohexyl-carbodiimide was dissolved in 1 ml of dioxane. The latter two solutions were mixed together and stirred for 30 minutes. Then 250 lamda of pyrene solution was transferred to the glass slurry solution. The slurry was stirred for two hours at room temperature and then allowed to stand at 4° C. overnight. The glass was washed four times with 10 ml phosphate buffer (pH=7.6) each wash, and was given two additional t-butanol washed with 10 ml phosphate buffer each time before testing. If necessary, the slurry was washed until no light could be detected from the supernate of the slurry. Then the 1-aminopyrene-antibody conjugate coated on the porous glass was tested by reacting with oxalate and peroxide. It was found that only the glass particle glowed in faint blue color.

EXAMPLE XVII

Fluorescein isothiocyanate anti-human gamma-globulin conjugate was prepared as follows: 4 mg of fluorescein isothiocyanate thoroughly mixed in 10 ml 0.1 M potassium phosphate buffer of pH=9.0. 4 ml of anti-human gamma-globulin (protein concentration of 20 mg/ml) was then added to the fluorescein phosphate solution. The mixture was continuously stirred for one hour at 4° C. and allowed to stand at the same temperature for another 24 hours. Excess fluorescein was removed by extensive dialysis against 0.1 M potassium phosphate buffer of pH=7.2. During dialysis, 100 ml of buffer each time was used, and the buffer was changed every 2 hours for 5 times.

Gamma-globulin coated porous glass was prepared as follows: 50 mg of epoxy-glass (3000 Å) pore size) was prepared in the same way as described in Example IV. 2.5 mg m-sodium periodate was dissolved in 5 ml of deionized water. Glass was then added to this solution and stirred at room temperature for 2 hours. The glass was washed thoroughly with deionized water and then with 10 ml 0.1 M potassium phosphate pH=9.0 buffer and kept for one hour. The glass was then filtererd and was ready for coupling. 5 ml human gamma-globulin (protein concentration of 30 mg/ml) was diluted with 5 ml of 0.1 M, pH=9.0 phosphate buffer. The activated glass was then added to this solution and was stirred at 4° C. for 2 hours before being allowed to stand overnight at the same temperature. After reaction was completed, the glass was washed extensively with 0.1 M potassium phosphate buffer of pH=7.2 and then filtered for immediate use. 30 mg of human gamma-globulin coated porous glass was added to 0.5 ml of fluorescein-antihuman gamma-globulin conjugate. The slurry was incubated on 24 cycles of agitation/settling (60/90 seconds ratio). Excess antibody solution was decanted and the glass was washed with 0.01 M potassium phosphate buffer of pH=7.2 until no light was detected by testing the decanted buffer in oxalate/peroxide system.

The glass was then washed with 5 ml t-butanol and excess butanol was withdrawn. Green color light was observed on glass particles upon addition of oxalate and peroxide.

EXAMPLES XVIII–XXI

USE OF ENCAPSUALTED FLUORESCER AS A LABEL IN CHEMILUMINESCENT IMMUNOASSAYS

The following Examples are given to illustrate the preparation and use of encapsulated fluorescers as labels, and are in no way intended to limit the scope of the invention described herein.

EXAMPLE XVIII

Chemiluminescence and entrapment of hydrophillic fluorescer (Rhodamine B) in lipsome A chloroform solution of phosphatidylcholine (egg) cholesterol and phosphatidylethanoamine in molar ratio of 6:2:2 (total concentration about 26 mg) was placed into a 50 ml round bottom flask and the solvent evaporated on a rotary vacuum evaporator at room temperature. The lipid film was then purged with $N_2$. 2.0 ml of 0.01 M borate buffer, pH 8.5 containing Rhodamine B was added to the lipid film, the film was dislodged from the walls of the flask by vigorous shaking. The resulting emulsion liposome suspension was removed and was sonically treated for 5 minutes in ice bath employing an ultrasound generator.

The liposome solution was passed through a sepharose 6B column to separate the uniform single compartment liposomes from the multilameller ones. The uniform single compartment liposome fraction was again passed through G-75 sephadex column to remove free Rhodamine B.

25 μl 0.0144 M to TCPO (2,4,5-Trichlorophenyloxalate) in Glyme and 25 μl of 1.23 M $H_2O_2$ were pipetted into a 6×50 mm test tube. The liposome enclosed Rhodamine B solution was first treated with Triton X-100 (to release the Rhodamine B), 50 μl of this solution was then injected to the $H_2O_2$/oxalate mixture, light was detected by Pico-Lite luminometer with a red filter.

EXAMPLE XIX

Chemiluminescence and entrapment/embedding of hydrophobic fluorescer DAET (Dianisylethynyltetracene) in liposome A chloroform solution containing gangliosides, phosphatidylcholine, cholesterol (10:45:45 mole ratio) and 200 mM DAET was evaporated in rotary vacuum evaporator at room temperature. The lipid film was purged with $N_2$ and flooded with 2.0 ml of 0.010 M borate buffer pH 8.5. The lipid emulsion solution was then sonicated for five (5) minutes in an ice bath.

The liposome solution was first passed through Sepharose 6B column and again G-75 Sephadex column to separate undispersed lipids, multilameller liposomes and free fluorescer.

The liposome solution was treated with Triton X-100 to ensure the rupture of the lipid membrane. 25 μl of 0.0144 M TCPO and 25 μl of 1.2 3 M $H_2O_2$ were pipetted into a 6×50 mm test tube and the tube was loaded into the analyzer of Pico-Lite luminator. A 50 μl of the Triton X-100 treated liposome solution was injected into the test tube and the emission of light was detected by Pico-Lite luminometer with a red filter.

EXAMPLE XX

Chemiluminescence and entrapment of fluorescer (hydrophillic or hydrophobic) bound onto silica sol 0.5 ml silica sol of 5 nm size was diluted with 0.5 ml of 0.01 M borate buffer pH 12.5. 25 μl of γ-aminopropyltriethyoxysilane was then added to the sol solution. The mixture was then vigorously shaken to disperse the sole particles. The sol solution was then dialyzed extensively against deionized water pH=9.0. LRSC (lissamine Rhodamine sulfonyl chloride) 5 mg in 1.0 ml 0.01 M borate pH=12.5 was then added to the sol solution and incubated overnight. The Rh-B/sol was then separated from free fluorescer by either dialysis or gel filtration. The fluorescent sol was then dispersed in borate buffer and enclosed by liposome as indicated in Example XIX.

The entrapped Rh-B/sol was treated with Triton X-100, and the solution was then injected to a mixture of TCPO/$H_2O_2$. Light was detected from Pico-Lite luminometer with a red filter.

EXAMPLE XXI

Chemiluminescent immunoassay utilizing liposome entrapped fluorescer as a label

20 μl of 25% glutaraldehyde was added to 2 ml liposome containing Rhodamine B as prepared in Example XVIII and incubated at 20° C. for 10 minutes. Excess glutaraldehyde was dialyzed against 1 liter of 0.145 M NaCl for 1 hour and again 1 liter of borate buffer for another hour at room temperature. The activated liposome was then incubated with Anti-$Hb_sAg$ solution at 4° C. overnight.

After incubation, the liposome conjugated with antibody was purified by passing through a separose 4B column.

The immunoassay procedure was carried out by using the reagents of RIAUSURE kit with the liposome conjugated antibody replacing the $I^{125}$ labelled antibody. Triton X-100 solution was added to the test tube after the biological assay and before the addition of $TCPO/H_2O_2$ solution. Light was generated by positive sample and detected by Pico-Lite luminator with a red filter.

The preferred energy source for carrying out the method of the present invention is that generated by the reaction of a peroxide and an oxalate/oxamide selected from the group comprising bis(2,4,6-trichlorophenyl)oxalate,
bis(3-trifluoro methyl-4-nitrophenyl)oxalate,
bis(2-formyl-4-nitrophenyl)oxalate,
bis(2,6-dichloro-4-nitrophenyl)oxalate,
N,N'-bis(2,4,5-trichlorophenyl)-N,N'-bis(trifluoromethyl sulfonyl)oxamide,
N,N'-bis(2,4-dichlorophenyl)-N,N'-bis(trifluoromethyl sulfonyl)oxamide,
N,N'-bis(2-methoxy ethyl)-N,N'-bis(trifluoromethyl sulfonyl)oxamide,
and N,N'-bis(4-nitro phenyl)-N,N-bis(trifluoro methyl sulfonyl)oxamide.

Although the above examples illustrate various modifications of the present invention, other variations will suggest themselves to those skilled in the art in the light of the above disclosure. It is to be understood, therefore, that changes may be made in the particular embodiments described above which are within the full intended scope of the inventions as defined in appended claims.

We claim:

1. A system for the detection of a biological analyte of interest which comprises a microencapsulated fluorescer material which has been conjugated to an immunological specie specific to the biological analyte of interest, a means of disrupting the capsule containing the fluorescer and an energy source other than electro-magnetic radiation which is capable of activating the fluorescer.

2. A system for the detection of a biological analyte of interest according to claim 1 which comprises a microencapsulated fluorescer which has been conjugated to an immunological specie specific to the biological analyte of interest, a means of disrupting the capsule containing the fluorescer and an excess of an energy source other than electro-magnetic radiation which is capable of activating the fluorescer.

3. A method for the qualitative detection of a biological analyte of interest comprising:
(a) labeling an immunological specie specific to the analyte of interest with a microencapsulated fluorescer material which is biologically compatible with such specie;
(b) contacting the specie labeled by the microencapsulated fluorescer and the biological analyte of interest to form a specie labeled by a microencapsulated fluorescer/biological analyte complex;
(c) separating the specie labeled by a microencapsulated fluorescer/biological analyte complex;
(d) disrupting the capsule containing the fluorescer label thus freeing it to solution;
(e) contacting the freed fluorescer with an energy source other than electro-magnetic radiation which is capable of activating the fluorescer label; and
(f) determining the presence of chemiluminescent light emitted.

4. A quantitative method for measuring the amount of a biological analyte of interest comprising:
(a) labeling an immunological specie specific to the analyte of interest with a microencapsulated fluorescer material which is biologically compatible with such specie;
(b) contacting the specie labeled by the microencapsulated fluorescer and the biological analyte of interest to form a specie labeled by a microencapsulated fluorescer/biological analyte complex;
(c) separating the specie labeled by a microencapsulated fluorescer/biological analyte complex;
(d) disrupting the capsule containing the fluorescer label thus freeing it to solution;
(e) contacting the freed fluorescer with an energy source other than electro-magnetic radiation which is capable of activating the fluorescer label; and
(f) measuring the quanta of chemiluminescent light emitted.

5. The method of claim 3 wherein the microencapsulated fluorescer material of (a) is chemically conjugated to the immunological specie specific to the biological of interest.

6. The method of claim 5 wherein the chemical conjugation of the encapsulated fluorescer material to the immunological specie specific to the biological of interest is carried out in such a way as to prevent substantial biological damage to the attached specie.

7. The method of claim 3 wherein the microencapsulated fluorescer material utilized has a spectral emission of from about 350 millimicrons to about 1000 millimicrons.

8. The method of claim 3 wherein the microencapsulated fluorescer material utilized has a spectral emission above the emission wavelength of the immunological specie specific to the biological of interest, the energy source, or any solvent system utilized.

9. The method of claim 3 wherein the microencapsulated fluorescer material utilized has been formed in such a manner as to produce a microcapsule having a high concentration of fluorescer material.

10. The method of claim 3 wherein the microencapsulated fluorescer material utilized has a microcapsule structure having one or more reactive groups to enable the microcapsule's conjugation with an immunological specie specific to the analyte of interest.

11. The method of claim 3 wherein the microencapsulated fluorescer material utilized possesses a microcapsule of uniform colloidal size whose structure has a membrane which is easily disrupted to free the fluorescer material.

12. The method of claim 3 wherein the microencapsulated fluorescer material utilized is selected from the group consisting of 5,12-dihydro quinoxalo (2,3,6) phenazine, magnesium and zinc metalo porphyrins, neutral red, magdalla red, acridine red, acridine orange, dianisyl ethynyl tetracene, phenizine, rhodamine, 3,4,9,10 perylene tetracarboxylic dianhydride, and derivatives thereof.

13. The method of claim 3 wherein the energy source of (e) which is contacted with the freed fluorescer material is present in excess of the amount required to activate all of the freed fluorescer material.

14. The method of claim 3 wherein the energy source of (e) is any source other than electro-magnetic radiation which is capable of activating the particular fluorescer selected.

15. The method of claim 3 wherein the energy source of (e) is the reaction product of a peroxide and an oxalate/oxamide selected from the group consisting of
bis(2,4,6-trichlorophenyl)oxalate,
bis(3-trifluoro methyl-4-nitrophenyl)oxalate,
bis(2-formyl-4-nitrophenyl)oxalate,
bis(2,6-dichloro-4-nitrophenyl)oxalate,
N,N'-bis(2,4,5-trichlorophenyl)-N,N'-bis(trifluoromethyl sulfonyl)oxamide,
N,N'-bis(2,4-dichlorophenyl)-N,N'-bis(trifluoromethyl sulfonyl)oxamide,
N,N'-bis(2-methoxy ethyl)-N,N'-bis(trifluoromethyl sulfonyl)oxamide,
and N,N'-bis(4-nitro phenyl)-N,N'-bis(trifluoro methyl sulfonyl)oxamide.

16. A method according to claim 14 wherein the energy source is a chemical reaction selected from the group consisting of 2-napthol-3,6,8-trisulfonic acid, 2-carboxyphenyl, 2-carboxy-6-hydroxyphenol, 1,4-dihydroxy-9, 10-diphenylanthracene, 2-napthol, luminol, lophine, pyrogallol, luciferin, dioxetanes, dioxetane-ones, and other peroxide reactions.

17. A method according to claim 14 wherein the energy source is derived from a chemical reaction, ozone, an electrical current, an electro-chemical reaction, or a mechanically generated species.

18. The method according to claim 3 which is carried out utilizing an assay technique.

19. The method according to claim 3 which is carried out utilizing a heterogeneous sandwich assay technique.

20. The method according to claim 3 which is carried out utilizing a heterogeneous competitive assay technique.

21. A system for the detection of a biological analyte of interest which comprises a microencapsulated quenching/poisoning material which has been conjugated to an immunological specie specific to the biological analyte of interest, a chemiluminescent reaction which generates an energy signal, and a means of disrupting the capsule containing the quencher/poison thereby liberating the quencher/poison to free solution and vitiating or diminishing the chemiluminescent reaction generated energy signal.

22. The method of claim 4 wherein the microencapsulated fluorescer material of (a) is chemically conjugated to the immunological specie specific to the biological of interest.

23. The method of claim 22 wherein the chemical conjugation of the microencapsulated fluorescer material to the immunological specie specific to the biological of interest is carried out in such a way as to prevent substantial biological damage to the attached specie.

24. The method of claim 4 wherein the microencapsulated material utilized has a spectral emission of from about 350 millimicrons to about 1000 millimicrons.

25. The method of claim 4 wherein the microencapsulated fluorescer material utilized has a spectral emission above the emission wavelength of the immunological specie specific to the biological of interest, the energy source, or any solvent system utilized.

26. The method of claim 4 wherein the microencapsulated fluorescer material utilized has been formed in such a manner as to produce a microcapsule having a high concentration of fluorescer material.

27. The method of claim 4 wherein the microencapsulated fluorescer material utilized has a microcapsule structure having one or more reactive groups to enable the microcapsule's conjugation with an immunological specie specific to the analyte of interest.

28. The method of claim 4 wherein the microencapsulated fluorescer material utilized possesses a microcapsule of uniform collodial size whose structure has a membrane which is easily disrupted to free the fluorescer material.

29. The method of claim 4 wherein the microencapsulated fluorescer material utilized is selected from the group consisting of 5,12 -dihydro quinoxalo (2,3,6) phenazine, magnesium and zinc metalo porphyrins, neutral red, magdalla red, acridine red, acridine orange, dianisyl ethynyl tetracene, phenizine, rhodamine, 3,4,9,10 perylene tetracarboxylic dianhydride, and derivatives thereof.

30. The method of claim 4 wherein the energy source of (e) which is contacted with the freed fluorescer material is present in excess of the amount required to activate all of the freed fluorescer material.

31. The method of claim 4 wherein the energy source of (e) is any source other than electro-magnetic radiation which is capable of activating the particular fluorescer selected.

32. The method of claim 4 wherein the energy source of (e) is the reaction product of a peroxide and an oxalate/oxamide selected from the group consisting of
bis(2,4,6 -trichlorophenyl)oxalate,
bis(3-trifluoro methyl-4-nitrophenyl)oxalate,
bis(2-formyl-4-nitrophenyl)oxalate,
bis(2,6-dichloro-4-nitrophenyl)oxalate,
N,N'-bis(2,4,5 -trichlorophenyl)-N,N'-bis(trifluoromethyl sulfonyl)oxamide,
N,N'-bis(2,4 -dichlorophenyl)-N,N'-bis(trifluoromethyl sulfonyl)oxamide,
N,N'-bis(2-methoxy ethyl)-N,N'-bis(trifluoromethyl sulfonyl)oxamide,
and N,N'-bis(4-nitro phenyl)-N,N'-bis(trifluoro methyl sulfonyl)oxamide.

33. A method according to claim 31 wherein the energy source is a chemical reaction selected from the group consisting of 2-napthol- 3,6,8-trisulfonic acid, 2-carboxyphenyl, 2-carboxy- 6 hydroxyphenol, 1,4-dihydroxy-9, 10-diphenylanthracene, 2-napthol, luminol, lophine, pyrogallol, luciferin, dioxetanes, dioxetaneones, and other peroxide reactions.

34. A method according to claim 31 wherein the energy source is derived from a chemical reaction, ozone, an electrical current, an electro-chemical reaction, or a mechanically generated species.

35. The method according to claim 4 which is carried out utilizing an assay technique.

36. The method according to claim 4 which is carried out utilizing a heterogeneous sandwich assay technique.

37. The method according to claim 4 which is carried out utilizing a heterogeneous competitive assay technique.

38. a microencapsulated fluorescer composition possessing a microcapsule structure having one or more reactive groups to enable the microcapsule's conjugation with an immunological specie specific to the analyte of interest.

39. A microencapsulated fluorescer composition useful in the labeling of an immunological specie specific to and for the detection of a biological of interest, wherein the fluorescer is selected from the group consisting of 5,12-dihydro quinoxalo (2,3,6) phenazine, magnesium and zinc metalo porphyrins, neutral red, magdalla red, acridine red, acridine orange, dianisyl ethynyl tetracene, phenizine, rhodamine, 3,4,9,10 perylene tetracarboxylic dianhydride, and derivatives thereof.

40. a conjugated microencapsulated fluorescer/immunological specie composition useful in the detection of a biological of interest which has been formed via reacting an immunological specie with a microencapsulated fluorescer possessing a microcapsule structure having one or more reactive groups to enable the microcapsule's conjugation with an immunological specie specific to the analyte of interest.

41. A conjugated microencapsulated fluorescer/immunological specie composition useful in the detection of a biological of interest which has been formed by reacting an immunological specie with an encapsulated fluorescer possessing a microcapsule of uniform colloidal size whose structure has a membrane which is easily disrupted to free the fluorescer material.

42. A conjugated microencapsulated fluorescer/immunological specie composition useful in the detection of a biological of interest which has been formed by reacting an immunological specie with a microencapsulated fluorescer selected from the group consisting of 5,12-dihydro quinoxalo(2,3,6) phenazine, magnesium and zinc metalo porphyrins, neutral red, magdalla red, acridine red, acridine orange, dianisyl ethynyl tetracene, phenizine, rhodamine, 3,4,9,10 perylene tetracarboxylic dianhydride, and dertivatives thereof.

43. A test kit for use in the detection of a biological of interest by means of an assay technique comprising, in a packaged combination, one or more containers holding
(1) a microencapsulated fluorescer material conjugated to an immunological specie specific to the biological of interest,
(2) a means for disrupting the membrane structure of the microencapsulated fluorescer, and
(3) chemical reagents capable of reacting to produce a high energy intermediate which will excite the freed fluorescer material to cause same to emit light.

44. The kit of claim 43 wherein the chemical reagents comprise (i) hydrogen peroxide or a chemical system for generating hydrogen peroxide and (ii) an oxamide or a bis-oxalate ester.

45. A test kit for use in the detection of a biological of interest by means of an assay technique comprising, in a packaged combination, one or more containers holding
(1) a microencapsulated quenching/poisoning material conjugated to an immunological specie specific to the biological of interest ,
(2) chemical reagents capable of reacting to produce a chemluminescent reaction generating an energy signal, and
(3) a means for disrupting the membrane structure of the microencapsulated quencher/poisoning material to liberate the quencher/poison to free solution.

46. A method for the qualitative detection of a biological analyte of interest comprising:
(a) labeling an immunological specie specific to the analyte of interest with a microencapsulated fluorescer material which is biologically compatible with such specie;
(b) contacting the specie labeled by the micro-encapsulated fluorescer and the biological analyte of interest to form a specie labeled by a microencapsulated fluorescer/biological analyte complex;
(c) disrupting the capsule containing the fluorescer label thus freeing it to solution;
(d) contacting the freed fluorescer with an energy source other than electro-magnetic radiation which is capable of activating the fluorescer label; and
(e) determining the presence of chemiluminescent light emitted.

47. A quantitative method for measuring the amount of a biological analyte of interest comprising:
(a) labeling an immunological specie specific to the analyte of interest with a microencapsulated fluorescer material which is biologically compatible with such specie;
(b) contacting the specie labeled by the microencapsulated fluorescer and the biological analyte of interest to form a specie labeled by a microencapsulated fluorescer/biological analyte complex;
(c) disrupting the capsule containing the fluorescer label thus freeing it to solution;
(d) contacting the freed fluorescer with an energy source other than electro-magnetic radiation which is capable of activating the fluorescer label; and
(e) measuring the quanta of chemiluminescent light emitted.

* * * * *

UNITED STATES PATENT AND TRADEMARK OFFICE
CERTIFICATE OF CORRECTION

PATENT NO. : 4,372,745
DATED : February 8, 1983
INVENTOR(S) : RICHARD M. MANDLE and YUAN N. WONG It is certified that error appears in the above—identified patent and that said Letters Patent is hereby corrected as shown below:

Column 15, line 20, "metallo-orgnic" should read
-- metallo-organic --.

Column 19, line 6, "assy" should read -- assay --.

Column 20, line 4, "(500 A pore size)" should read
--(500 Å pore size)--.

Column 22, line 12, "methanol," should read -- methanol. --.

Column 22, line 65, "coatd" should read -- coated --.

Column 24, line 15, "sets forth in the" should read
-- sets forth the --.

Column 25, line 58, "N$_2$.2.0 ml" should read -- N$_2$.  2.0ml --.

Signed and Sealed this

Thirty-first Day of May 1983

[SEAL]

Attest:

DONALD J. QUIGG

Attesting Officer    Acting Commissioner of Patents and Trademarks